(12) United States Patent
Niino et al.

(10) Patent No.: US 6,252,235 B1
(45) Date of Patent: Jun. 26, 2001

(54) APPARATUS FOR IMAGING FLUORESCENT PARTICLES

(75) Inventors: Masao Niino; Hiroki Matsui; Akio Komatsu, all of Gamagori (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 09/213,763

(22) Filed: Dec. 17, 1998

(30) Foreign Application Priority Data

Dec. 25, 1997 (JP) ................................... 9-356415

(51) Int. Cl.$^7$ ................................... G01N 21/01
(52) U.S. Cl. ................................... 250/458.1; 250/459.1; 250/227.22
(58) Field of Search ................................... 250/458.1, 459.1, 250/227.22

(56) References Cited

U.S. PATENT DOCUMENTS

| | | | |
|---|---|---|---|
| Re. 32,598 | 2/1988 | White | 356/301 |
| 5,225,164 | 7/1993 | Astle | 356/440 |
| 5,355,215 | 10/1994 | Schroeder et al. | 356/317 |
| 5,424,841 | * 6/1995 | Van Gelder et al. | 250/458.1 |
| 5,428,451 | * 6/1995 | Lea et al. | 250/458.1 |
| 5,436,717 | * 7/1995 | Ogino | 250/458.1 |
| 5,457,527 | 10/1995 | Manns et al. | 356/246 |
| 6,071,748 | * 6/2000 | Modlin et al. | 250/459.1 |
| 6,097,025 | * 8/2000 | Modlin et al. | 250/227.22 |

* cited by examiner

Primary Examiner—Constantine Hannaher
Assistant Examiner—Otilia Gabor
(74) Attorney, Agent, or Firm—Adams & Wilks

(57) ABSTRACT

An apparatus for imaging fluorescent particles comprises an imaging vessel having a lower section defining an interior space for containing fluorescent particles, the lower section having a side wall, a bottom wall and an exterior surface portion defining an entry surface for transmitting into the interior space a flat excitation beam of light. A light projecting device projects a flat excitation beam of light onto the entry surface of the imaging vessel in a direction generally parallel to the bottom wall thereof to illuminate the fluorescent particles. Images of the illuminated fluorescent particles are captured from the bottom wall of the imaging vessel.

23 Claims, 9 Drawing Sheets

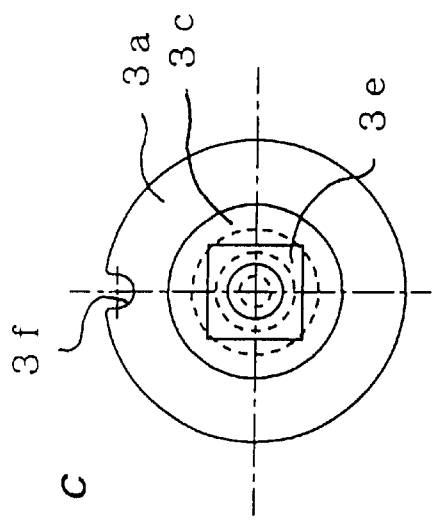
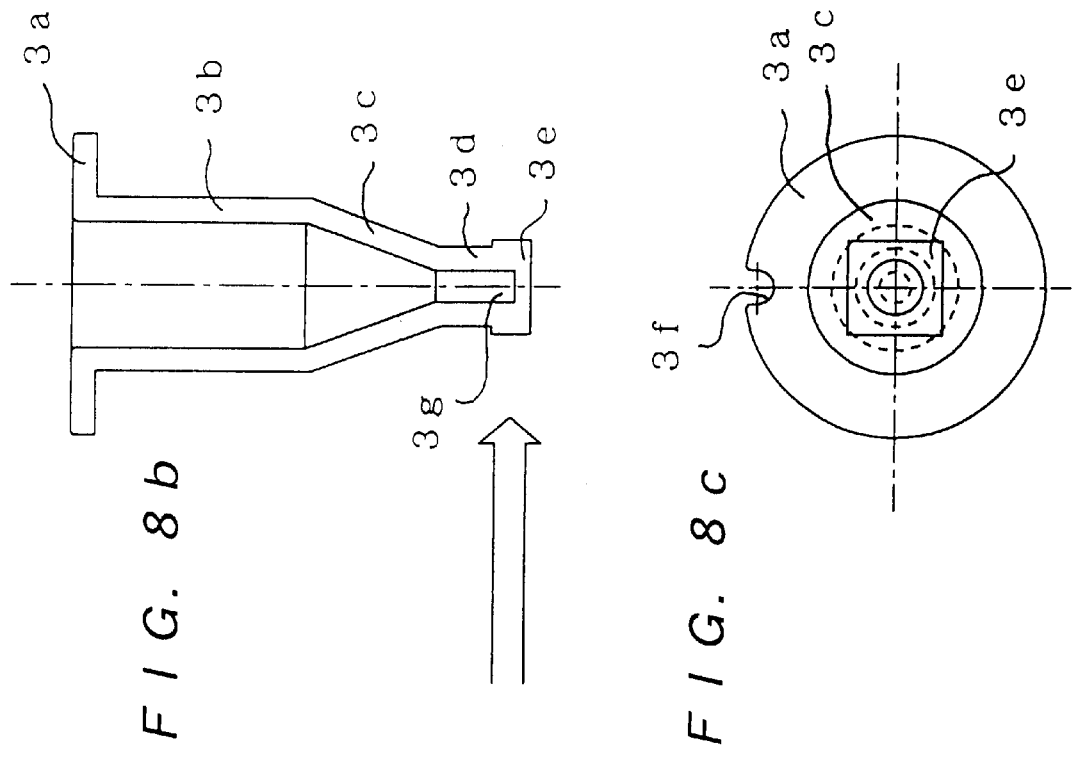
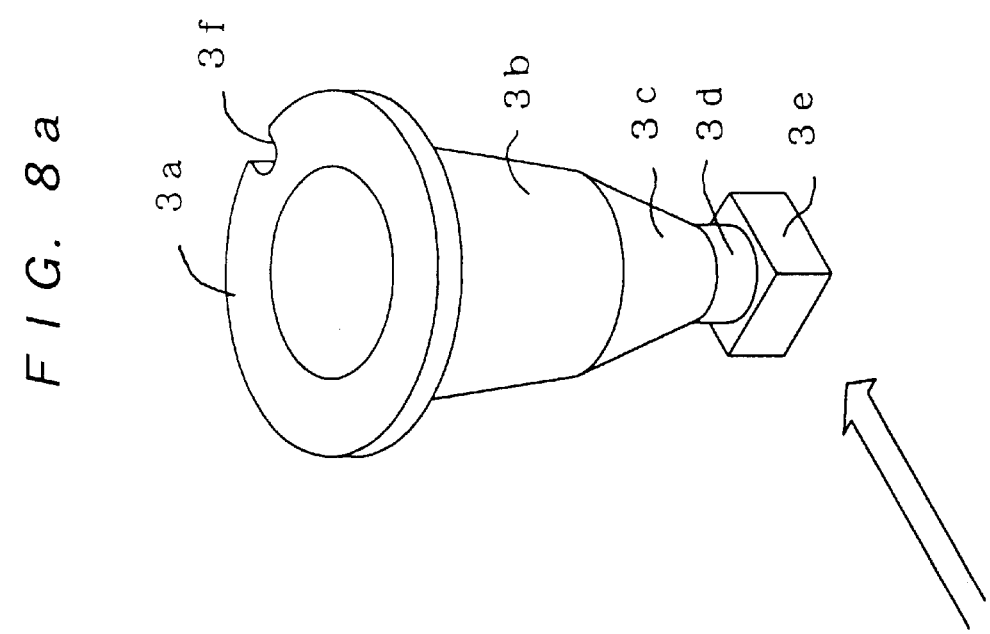
FIG. 8a
FIG. 8b
FIG. 8c

APPARATUS FOR IMAGING FLUORESCENT PARTICLES

BACKGROUND OF THE INVENTION

1. Field of the Invention

This invention relates to an apparatus for imaging fluorescent particles, and more particularly to an apparatus for imaging fluorescent particles such as leukocytes or the like stained with a fluorescent dye.

2. Description of the Prior Art

In the medical field, platelet preparations and erythrocyte preparations are produced by extracting platelets and erythrocytes from whole blood. These platelet and erythrocyte preparations are each used for blood transfusions, and it is undesirable for either preparation to contain leukocytes. It is therefore important to be able to know how many leukocytes the preparations contain. Conventionally this is done by placing a sample platelet preparation in a NAGEOTTE chamber, staining with a fluorescent dye, projecting an excitation light onto the sample and counting leukocytes via a microscope. Specifically, a 50 microliter sample is taken from a 200 or 400 milliliter bag of platelet preparation, the leukocytes in the sample are counted and converted to a leukocytes count for the whole bag. This is a tiring, inefficient, time-consuming task that has to be done by skilled personnel.

An apparatus has been proposed to enable leukocytes to be counted, instead, by staining the leukocytes with a fluorescent dye, illuminating the sample with an excitation light having predetermined wavelengths, using a CCD camera or the like to image the sample and then analyzing the images to obtain a count of the leukocytes. However, the solution containing the stained leukocytes also contains fluorescent dye that also emits fluorescent light. Thus, since not only the stained leukocytes but also the fluorescent dye itself is excited by the excitation light, there is a marked decrease in the contrast of the leukocytes that it is desired to observe or image. In some cases, the contrast may worsen to the point that the leukocyte images become so buried in the background that they cannot be picked out, making it impossible to count the leukocytes.

An object of the present invention is to provide an apparatus for imaging fluorescent particles that enables the fluorescent particles to be well imaged by reducing the effect of background light.

SUMMARY OF THE INVENTION

To attain the above object, the present invention provides an apparatus for imaging fluorescent particles stained with a fluorescent dye, comprising an imaging vessel for collecting and accommodating the fluorescent particles in a bottom portion thereof, means for generating an excitation light for exciting the fluorescent particles, illumination means for illuminating only a vicinity of the bottom portion of the imaging vessel by the excitation light, and means for obtaining images from below the bottom portion of the imaging vessel.

In accordance with this arrangement, as the fluorescent particles that are the object of interest are accumulated in the bottom part of the imaging vessel and the excitation light is projected on just that bottom part of the vessel, it is possible to reduce background light and thereby improve the contrast of the images obtained.

As a means that can be used to ensure that just the bottom portion of the vessel is illuminated, a cover can be positioned to prevent the upper part of the imaging vessel from being illuminated by the excitation light, or the same effect can be obtained by using a cover with a slit-shaped aperture.

In such a case, the fluorescent particles can be illuminated even more effectively by using a cylindrical lens or the like to convert the thin excitation laser beam into a wide, flat beam in order to illuminate just the bottom portion of the vessel. The same effect can also be obtained by deflecting the excitation light along the bottom portion, or by projecting the excitation light via a bundle of optical fibers the exit end of which is arranged in a straight line.

Thus markedly reducing the amount of background light allows the fluorescent particles to be imaged with high contrast, thereby increasing the reliability of the fluorescent particle count.

Further features of the invention, its nature and various advantages will become more apparent from the accompanying drawings and following detailed description of the invention.

BRIEF DESCRIPTION OF THE DRAWINGS

FIG. 8a is an exterior perspective view of the imaging vessel.

FIG. 8b is a cross-sectional view of the vessel.

FIG. 8c is a bottom view of the vessel.

DETAILED DESCRIPTION OF THE PREFERRED EMBODIMENTS

Figure 1:
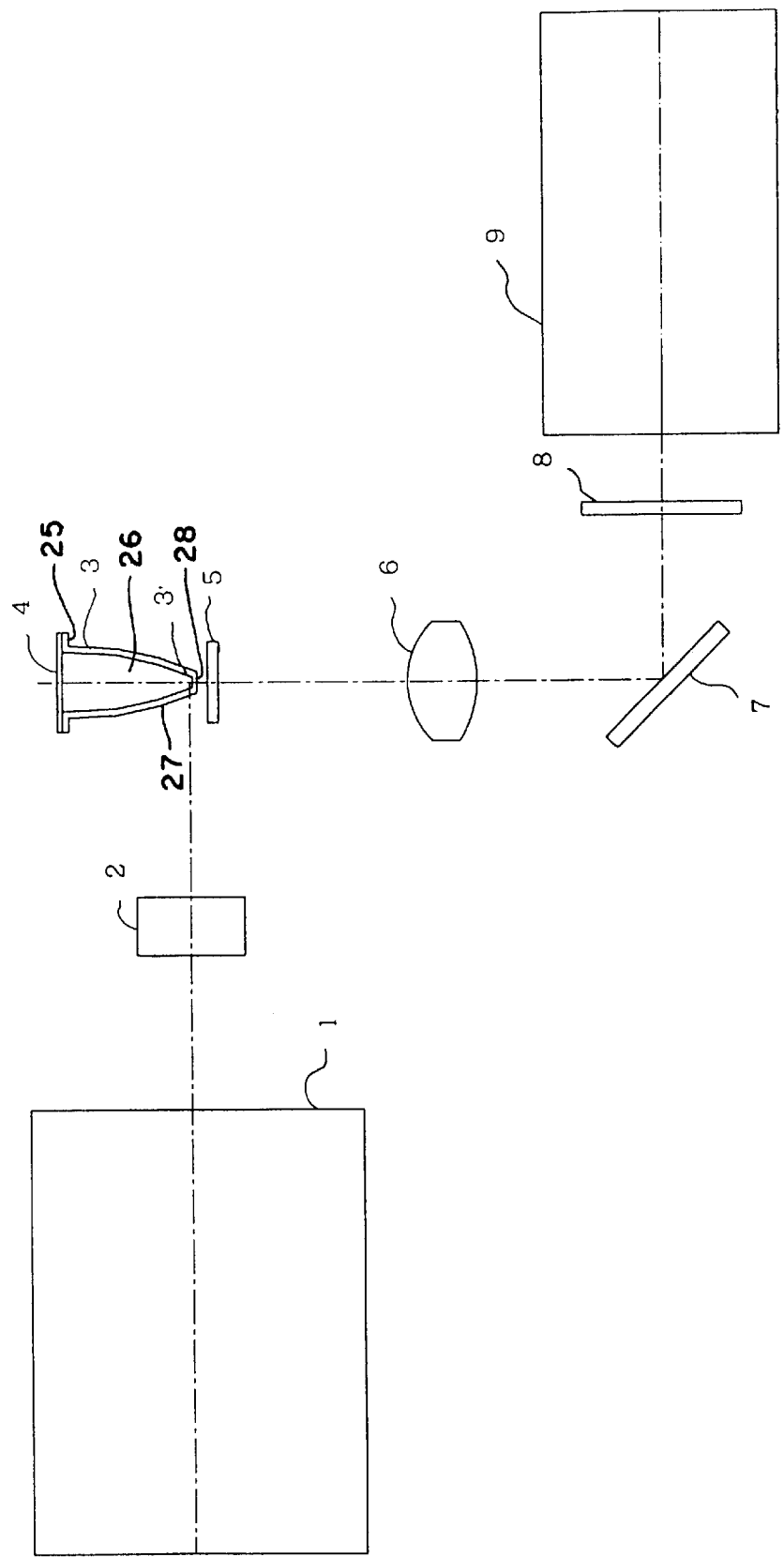
FIG. 1 is a block diagram showing the general configuration of an apparatus for imaging fluorescent particles according to the present invention.
Figure 2:
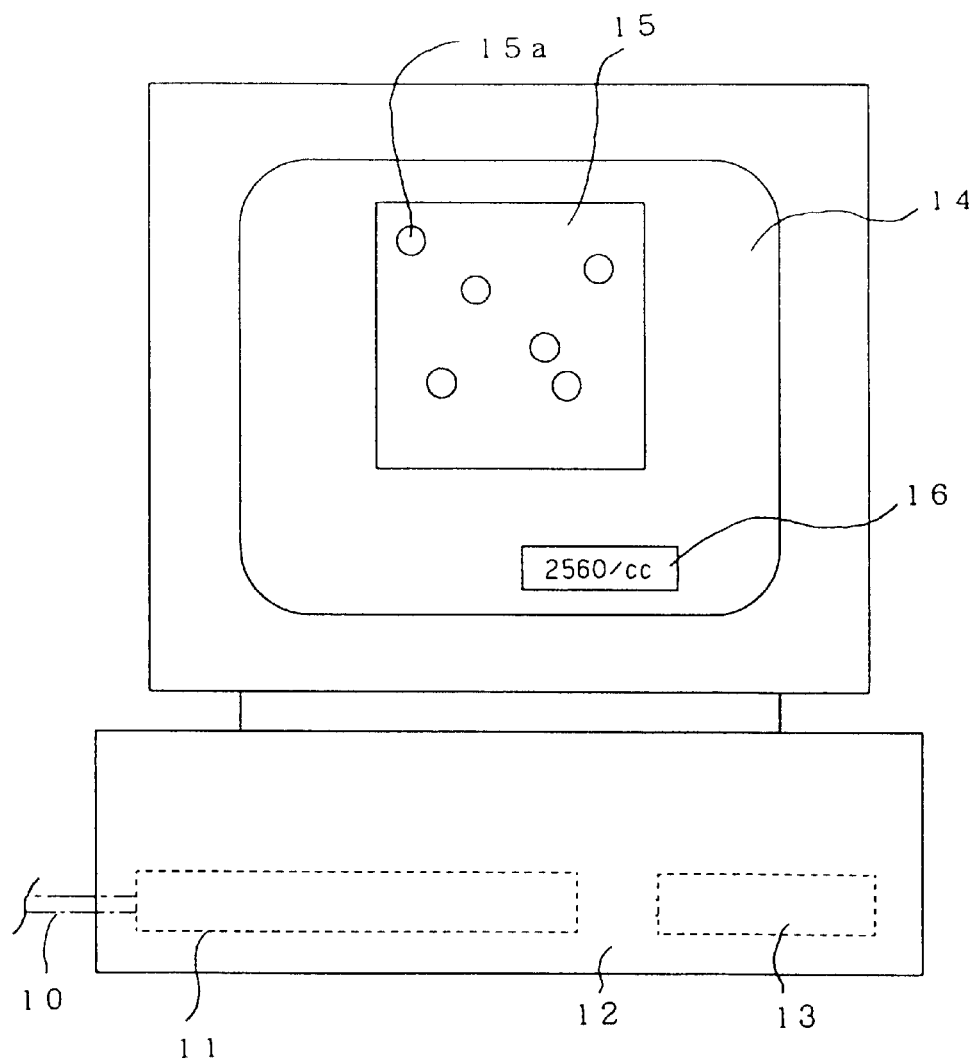
FIG. 2 is a front view of the apparatus used for analyzing and displaying obtained fluorescent particle images.

FIGS. 1 and 2 show the arrangement of a first embodiment of the present invention. In the drawings, reference numeral 1 denotes a laser light source, such as, for example, a YAG laser that produces a green laser beam. The laser beam from the laser light source 1 impinges upon, and is diffused by, a diffusion plate 2 comprised of ground glass or other such member that is able to diffuse light. The light thus diffused is projected at a bottom section or portion 3' of an imaging vessel 3, which has a generally tubular body the upper section or part 25 of which is covered by a cover 4. The bottom portion 3' has a side wall 27 and a bottom wall 28. Fluorescent particles are accumulated in an interior space 26 at the bottom portion of the imaging vessel 3, and these fluorescent particles fluoresce when illuminated by the laser beam. The images of the fluorescent particles illuminated by the laser beam pass via a cover-glass 5 and objective lens 6 to a mirror 7 that reflects the images to a barrier filter 8 that transmits light in a prescribed frequency band, and are then picked up by a CCD camera 9.

The images of the fluorescent particles picked up by the CCD camera 9 are passed via a signal line 10 to a video capture device 11 of a computer 12, where they are processed by an image processing circuit 13 (FIG. 2) to enable the fluorescent particles to be recognized. There is a change in brightness where there is a fluorescent particle, so the fluorescent particles can be recognized by, for example, using the differentiation of signal values to detect the positional coordinates of the particles. The fluorescent particles thus recognized are displayed on a monitor 14. FIG. 2 depicts the image 15 of the bottom portion of the vessel together with a plurality of fluorescent particles 15a therein, displayed on the monitor 14. The fluorescent particles 15a are counted and the count is also displayed at the lower part 16 of the monitor 14.

The imaging vessel 3 is molded in one piece from transparent polystyrene resin, glass, or acrylic resin, preferably polystyrene resin. Inserted into the imaging vessel 3 are a platelet preparation sample (100 microliters, for example), a chemical (Triton X) that dissolves platelet and leukocyte cytoplasm, and a fluorescent dye (propidium iodide) for staining leukocyte nuclei. The imaging vessel 3 is then subjected to centrifugal separation in a centrifuge (not shown), causing the leukocyte nuclei to collect in the bottom portion of the imaging vessel 3. All of the leukocyte nuclei can be collected in the bottom portion 3' of the imaging vessel 3 by applying a prescribed centrifugal force.

The cover 4 is then used to cover the imaging vessel 3 in which the leukocyte nuclei stained with a fluorescent dye are collected in the bottom portion 3' thereof, and the imaging vessel 3 is mounted on the imaging apparatus. For imaging, the laser light source 1 is activated, producing a laser beam which is diffused by the diffusion plate 2 and projected onto the bottom portion 3' of the imaging vessel 3. As the nuclei of the leukocytes in the bottom portion 3' of the imaging vessel 3 have been stained with a fluorescent dye, when they are illuminated by the beam of excitation light, they emit fluorescent light having a frequency of around 600 nm. This is picked up via the cover-glass 5, objective lens 6, mirror 7 and barrier filter 8 below the imaging vessel 3. The barrier filter 8 only transmits light having the frequency of fluorescent light, allowing light of harmful frequencies to be blocked at this point.

The laser beam is projected only at the bottom portion of the vessel, effectively illuminating the leukocytes collected there. Therefore, even if there is fluorescent dye floating in the solution in the imaging vessel 3, it is possible to prevent the fluorescent dye from forming harmful background light, thereby enabling the images to be obtained with improved contrast.

With reference to FIG. 2, the images of fluorescent particles thus obtained by the CCD camera 9 are passed via a signal line 10 to a video capture device 11 of a computer 12, where they are processed by an image processing circuit 13 to count the number of leukocytes 15a.

Figure 3:
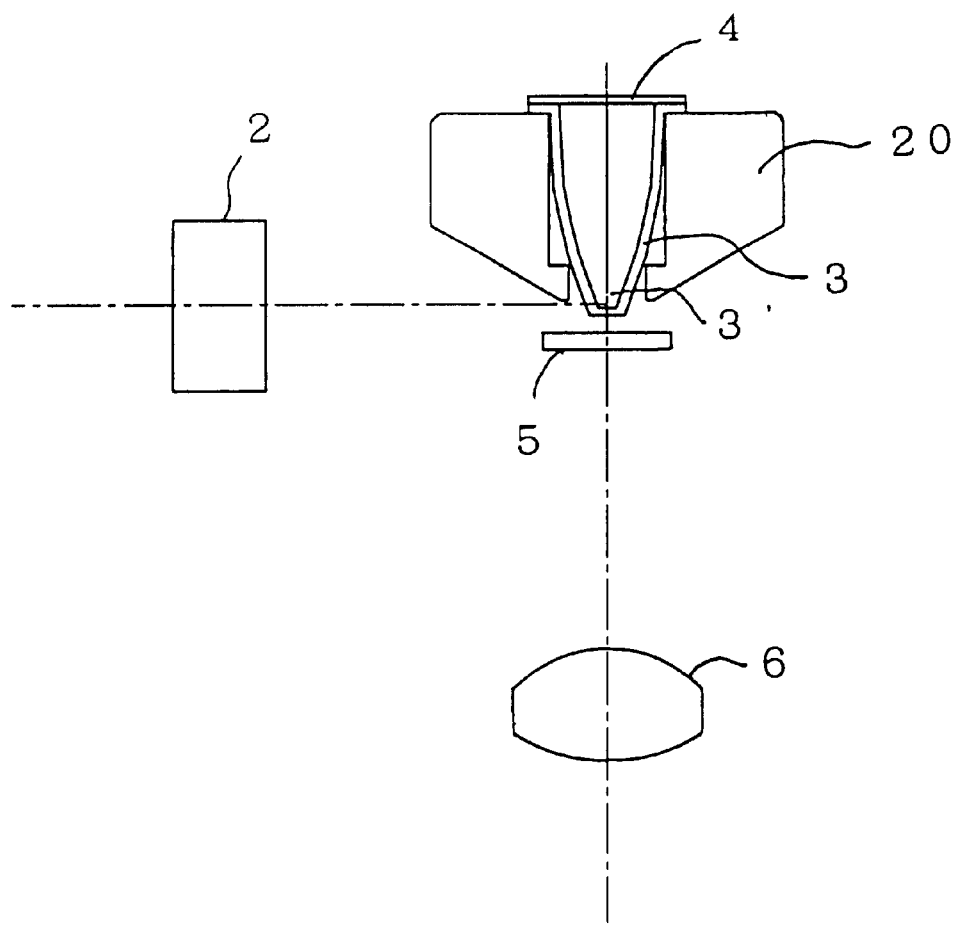
FIG. 3 is a diagram illustrating an arrangement of a cover used to shield the upper part of the imaging vessel.

In accordance with the arrangement described above, the laser beam is projected only onto the bottom portion of the imaging vessel and does not illuminate the upper part of the vessel. As shown by FIG. 3, the effect of only illuminating the bottom portion can be enhanced by providing a cover 20 that shields all parts other than the bottom portion from the illuminating light beam.

Figure 4:
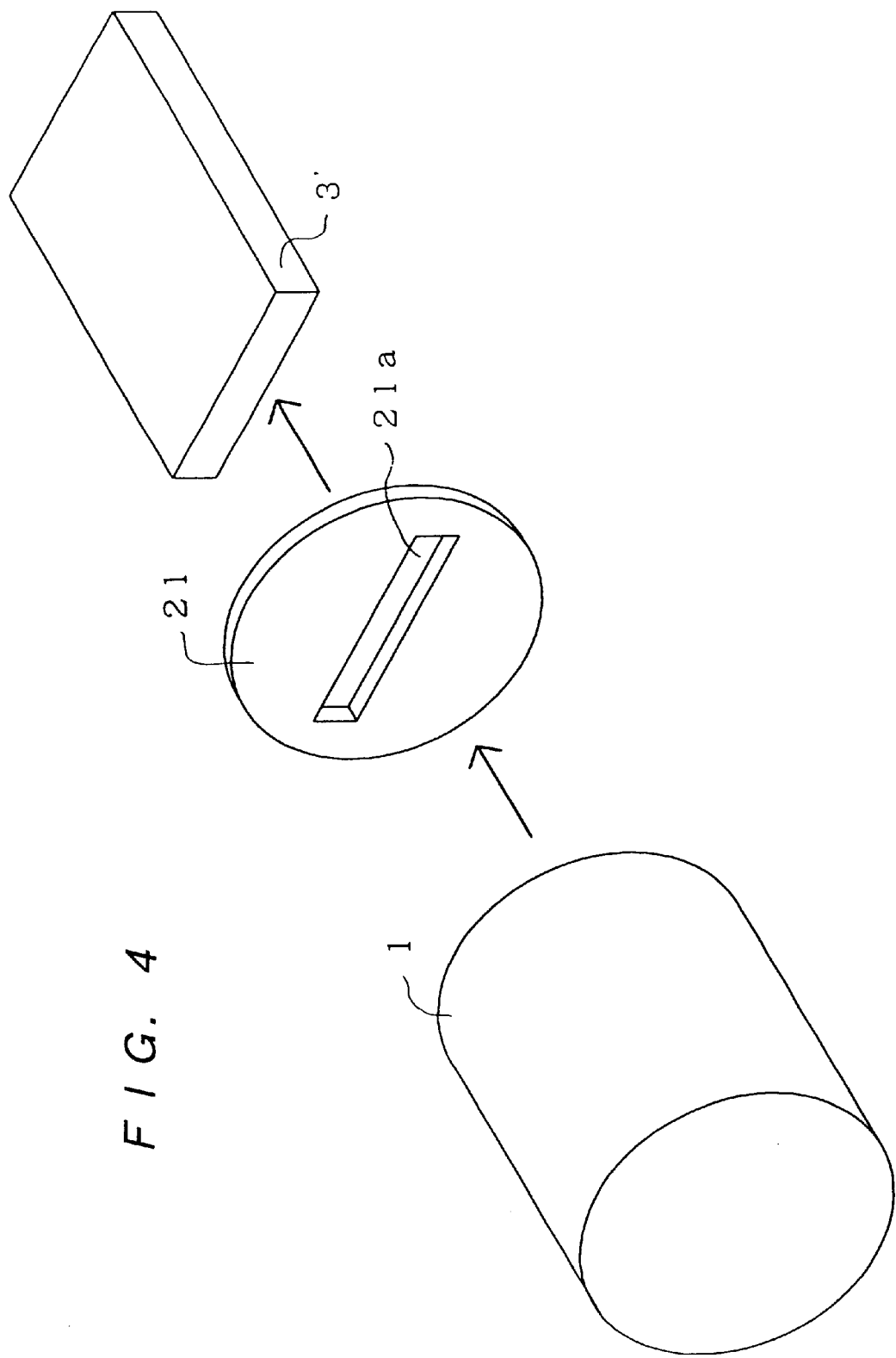
FIG. 4 is a diagram illustrating another arrangement for shielding the upper part of the imaging vessel from illuminating light.

Instead of the cover arrangement of FIG. 3, an arrangement such as that shown in FIG. 4 may be used. In this arrangement, a mask 21 having a central slit-shaped aperture 21a is used. The laser beam from the laser light source 1 passes through the aperture 21a, ensuring that only the bottom portion 3' of the imaging vessel 3 is illuminated.

Figure 5:
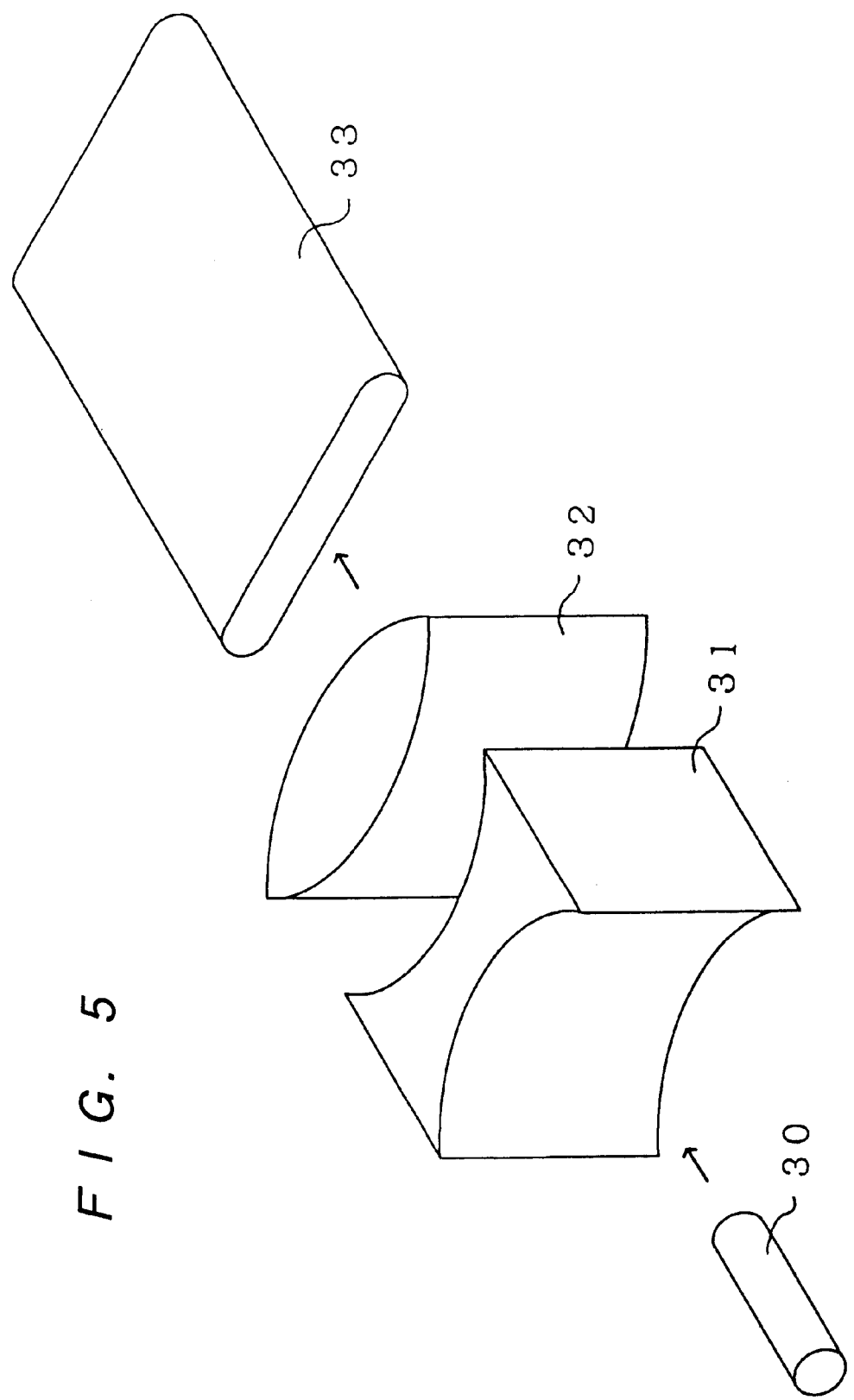
FIG. 5 is a diagram of an optical system used to form a strip-shaped excitation light beam.

A linear or line-shaped light beam would illuminate more of the bottom portion of the imaging vessel than a spot-shaped beam. FIG. 5 shows the type of arrangement that could be used in such a case, with laser beam 30 being shaped to a flat beam 33 by passage through cylindrical lenses 31 and 32, and the flat beam 33 being used to illuminate the bottom portion 3' of the imaging vessel 3 by projecting the flat beam 33 in a direction generally parallel to the bottom wall 28 of the bottom portion 3'.

Figure 6:
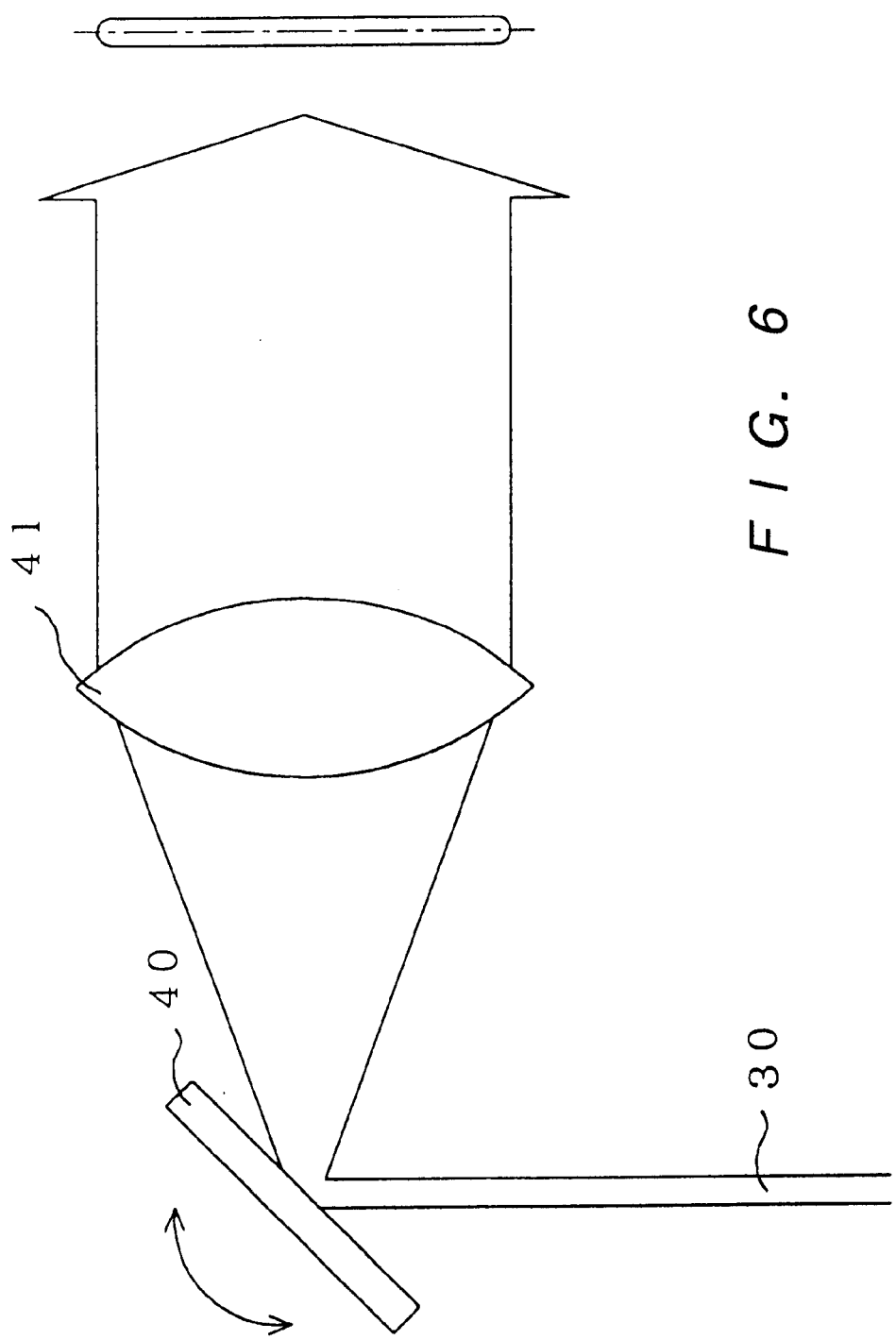
FIG. 6 is a diagram of another optical system used to form a strip-shaped excitation light beam.

FIG. 6 shows another arrangement, in which a scanning mirror 40 is used to deflect the laser beam 30, which passes through a lens 41 to scan the bottom portion of the imaging vessel.

Figure 7:
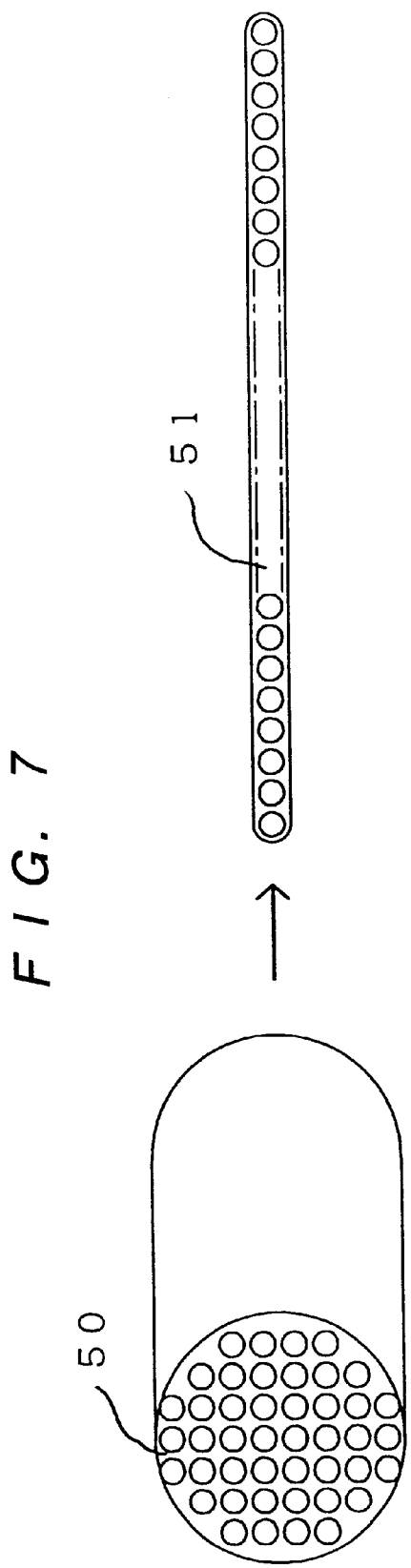
FIG. 7 is a diagram showing the configuration of optical elements used to form a strip-shaped excitation light beam.

FIG. 7 shows another arrangement, that uses a bundle of optical fibers. In this arrangement, the fibers at the entrance end 50 from which the laser beam enters are arranged in a round configuration, while at the exit end 51 the fibers are arranged in a straight line, with the exit end 51 being disposed in the vicinity of the bottom portion of the imaging vessel so as to illuminate the bottom portion thereof.

In each of these embodiments, only the bottom portion of the vessel, or the vicinity thereof, is illuminated, by a strip-shaped beam, thereby making it possible to obtain images of the fluorescent particles with good contrast. Moreover, if a diffusion plate 2 is used to diffuse the laser beam, it enables the bottom portion of the imaging vessel to be illuminated uniformly.

FIG. 8 shows a preferred embodiment of the imaging vessel 3, preferably formed as a one-piece molding of polystyrene resin. The vessel has a ringshaped upper portion 3a having a notch 3f for positioning purposes. The imaging vessel 3 comprises a cylindrical portion 3b that extends vertically downward from the upper portion 3a to a small-diameter portion 3d, via a sloping portion 3c. A substantially square or rectangular block portion 3e is formed at the lower end. One side of the block portion 3e is arranged to be illuminated by a laser beam, indicated by the arrow. When fluorescent particles are to be imaged, the imaging vessel 3 is attached to the apparatus, with the notch 3f being used to position the imaging vessel 3. When the vessel 3 has been fitted into position, a flat face of the block portion 3e is perpendicular to the direction of laser beam illumination, forming the entry surface for the incident beam. Thus, the laser beam illuminates only the bottom portion 3g of the imaging vessel 3.

Figure 9:
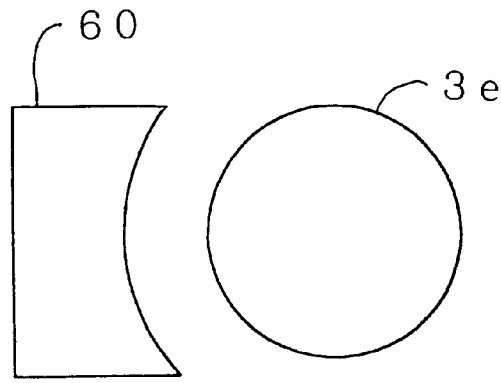
FIG. 9 is a cross-sectional horizontal view of an imaging vessel according to another configuration.

The bottom portion m ay also be illuminated by an arrangement such as the one shown in FIG. 9, in which the block portion 3e has a round cross-section, and a negative cylindrical lens 60 is disposed on the side from which the bottom portion is illuminated by the excitation beam.

Figure 10:
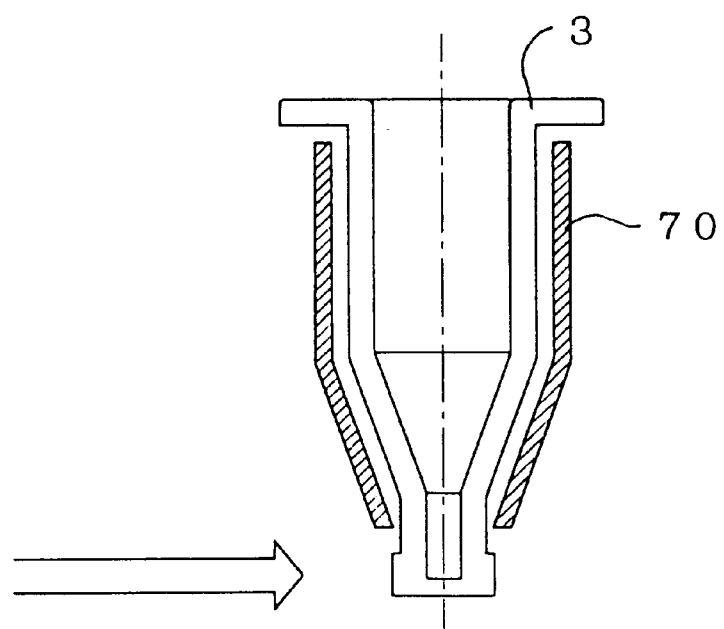
FIG. 10 is a cross-sectional view of an imaging vessel according to yet another configuration.

In the arrangement shown in FIG. 10, a cover 70 is used to shield parts of the imaging vessel 3 other than the bottom portion from the laser beam. In this case, the cover 20, shown in FIG. 3, on the imaging apparatus side may be omitted. The cover or shielding function may be realized by applying a light shield coating to the vessel, or by painting the vessel in a shielding color.

It is to be understood that while in the foregoing the invention has been described with reference to leukocytes as the fluorescent particles, the invention is not limited thereto but can be applied to other fluorescent particles.

As described in the foregoing, in accordance with the present invention, fluorescent particles to be imaged are collected in the bottom portion of an imaging vessel, only that bottom portion is illuminated by an excitation light beam, and the bottom portion is imaged from below. The result is that background light is reduced, making it possible to obtain high-contrast images of the fluorescent particles, thereby making it possible to evaluate the images of the fluorescent particles and count them with greater precision.

What is claimed is:

1. An apparatus for imaging fluorescent particles stained with a fluorescent dye, comprising:
    an imaging vessel having an interior space, an exterior surface, an upper portion, and a bottom portion having a side wall and a bottom wall for collecting fluorescent particles, a part of the exterior surface of the imaging vessel corresponding to the bottom portion defining an entry surface of the imaging vessel for receiving a flat excitation beam of light;
    light generating means for generating a flat excitation beam of light for exciting the fluorescent particles collected in the bottom portion of the imaging vessel;
    light projecting means for projecting the flat excitation beam of light generated by the light generating means onto the entry surface of the imaging vessel in a direction generally parallel to the bottom wall thereof to illuminate the fluorescent particles collected in the bottom portion of the imaging vessel; and
    means for capturing images of the illuminated fluorescent particles from the bottom wall of the imaging vessel.

2. An apparatus according to claim 1; further comprising a shielding member for covering exterior surface portions of the imaging vessel other than exterior surface portions thereof corresponding to the bottom portion.

3. An apparatus according to claim 1; further comprising a mask having a slit-shaped aperture; and wherein the light projecting means includes means for projecting the flat excitation beam of light through the slit-shaped aperture to illuminate only exterior surface portions of the imaging vessel in a vicinity of the bottom portion thereof.

4. An apparatus according to claim 1; wherein the light generating means includes a cylindrical lens for forming excitation light into the flat excitation beam of light; and wherein the light projecting means includes means for projecting the flat excitation beam of light to illuminate only exterior surface portions of the imaging vessel in a vicinity of the bottom portion thereof.

5. An apparatus according to claim 1; wherein the light projecting means includes scanning means for scanning the flat excitation beam of light along exterior surface portions of the imaging vessel in a vicinity of the bottom portion thereof.

6. An apparatus according to claim 1; wherein the light projecting means include a bundle of optical fibers having an exit end arranged in a straight line for illuminating only exterior surface portions of the imaging vessel in a vicinity of the bottom portion thereof.

7. An apparatus according to claim 1; wherein the light projecting means include an optical element for uniformly illuminating exterior surface portions of the imaging vessel in a vicinity of the bottom portion thereof.

8. An apparatus according to claim 7; wherein the optical element comprises is a diffusion plate.

9. An apparatus according to claim 1; wherein the bottom portion of the imaging vessel has side surfaces part of which define the entry surface of the imaging vessel.

10. An apparatus according to claim 9; wherein the bottom portion of the imaging vessel is generally square-shaped in cross-section and one side thereof forms the entry surface of the imaging vessel.

11. An apparatus according to claim 9; wherein the bottom portion of the imaging vessel has a generally round-shaped cross-section; and wherein the light projecting means includes a negative cylindrical lens disposed on a side of the entry surface of the imaging vessel.

12. An apparatus according to claim 9; wherein the bottom portion of the imaging vessel is generally rectangular-shaped in cross-section and one side thereof forms the entry surface of the imaging vessel.

13. An apparatus for imaging fluorescent particles comprising:
    an imaging vessel having a lower section defining an interior space for containing fluorescent particles, the lower section having a side wall, a bottom wall and an exterior surface portion defining an entry surface for transmitting into the interior space a flat excitation beam of light;
    light projecting means for projecting a flat excitation beam of light onto the entry surface of the imaging vessel in a direction generally parallel to the bottom wall thereof to illuminate the fluorescent particles; and
    means for capturing images of the illuminated fluorescent particles from the bottom wall of the imaging vessel.

14. An apparatus according to claim 13; further comprising a shielding member for covering exterior surface portions of the imaging vessel other than the exterior surface portion of the lower section.

15. An apparatus according to claim 13; further comprising a mask having a slit-shaped aperture; and wherein the light projecting means includes means for projecting the flat excitation beam of light through the slit-shaped aperture to illuminate only the exterior surface portion of the lower section of the imaging vessel.

16. An apparatus according to claim 13; further comprising light generating means for generating excitation light, the light generating means having a cylindrical lens for forming the excitation light into a flat excitation beam of light; and wherein the light projecting means includes means for projecting the flat excitation beam of light formed by the cylindrical lens to illuminate only the exterior surface portion of the lower section of the imaging vessel.

17. An apparatus according to claim 13; wherein the light projecting means includes scanning means for scanning the flat excitation beam of light along the exterior surface portion of the lower section of the imaging vessel.

18. An apparatus according to claim 13; wherein the light projecting means include a bundle of optical fibers having an exit end arranged in a straight line for illuminating only the exterior surface portion of the lower section of the imaging vessel.

19. An apparatus according to claim 13; wherein the light projecting means include an optical element for uniformly illuminating the exterior surface portion of the lower section of the imaging vessel.

20. An apparatus according to claim 19; wherein the optical element comprises is a diffusion plate.

21. An apparatus according to claim 13; wherein the lower section of the imaging vessel is generally square-shaped in cross-section and one side thereof forms the entry surface for transmitting the flat excitation beam of light into the interior space.

22. An apparatus according to claim 13; wherein the lower section of the imaging vessel is generally rectangular-shaped in cross-section and one side thereof forms the entry surface for transmitting the flat excitation beam of light into the interior space.

23. An apparatus according to claim 13; wherein the lower section of the imaging vessel has a generally round shaped cross-section; and wherein the light projecting means includes a negative cylindrical lens disposed on a side of the entry surface of the imaging vessel.

* * * * *